(12) United States Patent
Leckebusch

(10) Patent No.: US 9,517,463 B2
(45) Date of Patent: Dec. 13, 2016

(54) SYRINGE HAVING A MECHANICAL COUPLING PIECE

(71) Applicant: HAMILTON BONADUZ AG, Bonaduz (CH)

(72) Inventor: Klaus Leckebusch, Masein (CH)

(73) Assignee: HAMILTON BONADUZ AG, Bonaduz (CH)

( * ) Notice: Subject to any disclaimer, the term of this patent is extended or adjusted under 35 U.S.C. 154(b) by 0 days.

(21) Appl. No.: 14/897,792

(22) PCT Filed: Jun. 6, 2014

(86) PCT No.: PCT/EP2014/061912
§ 371 (c)(1),
(2) Date: Dec. 11, 2015

(87) PCT Pub. No.: WO2014/198673
PCT Pub. Date: Dec. 18, 2014

(65) Prior Publication Data
US 2016/0136637 A1    May 19, 2016

(30) Foreign Application Priority Data

Jun. 13, 2013  (DE) .................. 10 2013 210 998

(51) Int. Cl.
*B01L 3/02* (2006.01)
*A61M 5/34* (2006.01)

(52) U.S. Cl.
CPC .............. *B01L 3/0217* (2013.01); *B01L 3/022* (2013.01); *A61M 5/347* (2013.01); *A61M 5/348* (2013.01);
(Continued)

(58) Field of Classification Search
USPC ................................. 422/512, 524
See application file for complete search history.

(56) References Cited

U.S. PATENT DOCUMENTS 2,764,978 A    10/1956  James
3,563,373 A *  2/1971  Paulson ............... A61J 1/2093
                                                        206/229
(Continued)

FOREIGN PATENT DOCUMENTS

CN    1354022 A    6/2002
CN    102858395 A   1/2013
(Continued)

OTHER PUBLICATIONS

International Search Report issued in PCT/EP2014/061912 dated Sep. 1, 2014, 3 pages.
(Continued)

*Primary Examiner* — Jill Warden
*Assistant Examiner* — Brittany Fisher
(74) *Attorney, Agent, or Firm* — Rothwell, Figg, Ernst & Manbeck PC

(57) ABSTRACT

The invention relates to a syringe, comprising: a syringe body (12) having an axial inner cavity (16), which extends in the direction of a longitudinal axis (LA) of the syringe body (12) and in which a plunger (14) can be or is accommodated in such a way that the plunger can be moved in the longitudinal direction, and a needle (18), which can be or is connected to the syringe body (12) at a longitudinal end of the syringe body (12), wherein the syringe body (12) has a coupling segment (20) at the needle-side longitudinal end of the syringe body (12), to which coupling segment (20) the needle (18) can be or is fastened by means of a connecting element (22) that can be slid on in the longitudinal direction. According to the invention, at least one radially inward cavity (34) is provided on the coupling segment (20), which cavity can be brought into engagement or is in engagement with at least one corresponding locking segment (32) provided on the connecting element (22).

13 Claims, 3 Drawing Sheets

(52) U.S. Cl.
CPC ..... *B01L 2200/025* (2013.01); *B01L 2200/026* (2013.01); *B01L 2200/0689* (2013.01); *B01L 2300/0609* (2013.01); *B01L 2300/0672* (2013.01); *B01L 2300/12* (2013.01); *B01L 2400/0478* (2013.01)

(56) References Cited

U.S. PATENT DOCUMENTS

| | | | | |
|---|---|---|---|---|
| 3,820,652 | A * | 6/1974 | Thackston | A61M 5/002 206/365 |
| 3,901,413 | A * | 8/1975 | Harris, Sr. | B01L 3/022 222/309 |
| 3,916,893 | A * | 11/1975 | De Felice | A61M 5/2466 604/193 |
| 3,989,044 | A * | 11/1976 | Meierhoefer | A61M 5/3134 604/192 |
| 4,281,653 | A | 8/1981 | Barta et al. | |
| 4,424,057 | A * | 1/1984 | House | A61M 5/31596 604/88 |
| 4,490,142 | A * | 12/1984 | Silvern | A61M 5/344 604/241 |
| 4,615,468 | A * | 10/1986 | Gay | G21F 5/018 206/0.6 |
| 4,720,285 | A | 1/1988 | Pickhard et al. | |
| 4,740,205 | A * | 4/1988 | Seltzer | A61B 5/150587 604/192 |
| 4,781,701 | A | 11/1988 | Geprags | |
| 5,135,496 | A | 8/1992 | Vetter et al. | |
| 5,195,985 | A * | 3/1993 | Hall | A61B 5/1411 604/110 |
| 2005/0148947 | A1* | 7/2005 | Kadziauskas | A61M 5/284 604/240 |
| 2009/0163859 | A1 | 6/2009 | Lloyd et al. | |

FOREIGN PATENT DOCUMENTS

| | | |
|---|---|---|
| DE | 33 39 705 A1 | 5/1985 |
| DE | 20 2007 013 096 U1 | 4/2009 |
| EP | 0314696 B1 | 3/1992 |
| GB | 2 202 148 A | 9/1988 |
| GB | 2202148 A | 9/1988 |

OTHER PUBLICATIONS

First Office Action (with English translation) issued in Chinese Patent Application No. 201480033433.5, 13 pages (Jun. 30, 2016).
Search Report (with English translation) issued in Chinese Patent Application No. 201480033433.5, 3 pages (Jun. 21, 2016).

* cited by examiner a)

b)

SYRINGE HAVING A MECHANICAL COUPLING PIECE

CROSS REFERENCE TO RELATED APPLICATION

This application is a 35 U.S.C. 371 National Phase Entry Application from PCT/EP2014/061912, filed Jun. 6, 2014, which claims the benefit of German Patent Application No. 10 2013 210 998.9 filed on Jun. 13, 2013, the disclosure of which are incorporated by reference in their entirety.

The present invention concerns a syringe, in particular, a syringe for a dosing device used in chromatography applications such as high temperature chromatography or headspace chromatography.

Such a syringe comprises a syringe body having an axial inner cavity, which extends in the direction of a longitudinal axis of the syringe body and in which a plunger can be or is accommodated in such a way that the plunger can be moved in the longitudinal direction, and a needle, which can be or is connected to the syringe body at a longitudinal end of the syringe body, wherein the syringe body has a coupling segment at its needle-side longitudinal end of the syringe body, to which coupling segment the needle can be or is fastened by means of a connecting element that can be slid on in the longitudinal direction.

Such a syringe for use in laboratories is for example known from WO 2009/036994 A2. In the known syringe the needle and the syringe body are glued together by means of a hull-shaped guiding element, wherein the guiding element has an inner thread into which a tensioning screw that is connected to the needle can be screwed.

Further, also from medical science different couplings between needles and syringe bodies are known, which are, however, not sufficient for use in laboratories. In particular, these do not satisfy the requirements on stability and especially on leak tightness. Here, the problem arises that the purity of a fluid to be taken in or given off by the syringe cannot be guaranteed up to the desired degree.

It had turned out that gluing connections are disadvantageous for syringes for dosing devices used in laboratories, as during a use of such syringes in analyzing devices, such as (gas)-chromatography, a contamination of the probe in the syringe with, in particular, volatile organic materials stemming from the glue has occurred. These volatile materials outgas from the glue, if the syringe is warmed, and can influence the measurement results regarding the sample liquid obtained with the analyzing device significantly. Further, it is also difficult to use syringes with gluing connections in environments containing solvents, e.g. as sample fluid, as the used glues can be damaged by the solvents.

It is therefore an object of the invention to provide a syringe for a dosing device for which these disadvantages can be avoided.

To solve this problem it is proposed that in the aforementioned syringe at least one radially inwardly formed cavity is provided on the coupling segment, which cavity can be brought into engagement or is in engagement with at least one corresponding locking segment provided on the connection element.

The cavity on the coupling segment and the locking segment on the connection element allow a purely mechanical connection between needle and syringe body, which avoids the use of glue. Here, engagement of the locking segment into the cavity is obtained in a simple manner during axial slid on of the connecting element onto the coupling segment such that also manufacturing of such a syringe is simplified in comparison to manufacturing of a syringe with gluing connections and, if necessary, with a tension screw coupling between needle and connecting element.

It is preferable that the connecting element is formed as a hull that comprises a syringe body-side connecting segment and a needle-side supporting segment, wherein the at least one locking segment is arranged on the connecting segment.

To this end, it is proposed as further embodiment that on the connecting element several locking segments are provided, which are distributed in a circumferential direction and which extend along the inner circumference of the hull and point radially inwards.

It is further preferable that the connecting segment comprises in the region of the locking segments grooves that extend in the longitudinal direction and that begin at the syringe body-side end of the hull and point towards the needle-side end of the hull such that the locking segments comprise several locking segment parts that are arranged at a corresponding connecting segment parts, wherein the connecting segment parts can be deflected in a radial direction.

By such a construction the engagement between connecting element and coupling segment can be provided at several locations that are distributed around the circumference such that a secure, positive fitting connection can be guaranteed. By means of the (elastically) deflectable connecting segment parts the axial slid on of the connecting element onto the coupling segment is enabled, even if the locking segments or locking segment parts that point radially inwards reduce the inner diameter of the connecting piece in the region of the locking segment. The connecting segment parts lie during axial slid on onto the coupling segment against the locking segment parts on the coupling segment, wherein the connecting segment parts are deformed or bended in radial direction outwards until the locking segment parts or locking segments engage into the cavity on the coupling segment. In this process, the connecting segment parts move due to the elastic deformation radially inwards in a back-snapping manner.

To increase the leak tightness of the connection between syringe body and needle it is further proposed that the syringe comprises tensioning means, by which an axial pretension between coupling segment and connecting element can be or is produced, which acts onto sealing elements that are accommodated between the coupling segment and the connecting element.

To this end, it is conceived as a further embodiment that the tensioning means comprises the at least one cavity on the coupling segment, wherein the cavity extends along the circumference of the coupling segment and is formed as a thread.

Here, it is preferable that the thread is formed such that it comprises in both turning directions a transition to an outer circumferential surface of the coupling segment, and that preferably maximally one turn of the connecting element around the coupling segment is possible, preferably a partial turn around about ⅛ to ⅞ of the circumference of the coupling segment.

The proposed thread is not a usual thread, which effects the connection between two corresponding elements by a purely relative turning movement. In contrast, the thread, which is formed by the cavity on the coupling segment of the syringe, serves merely for providing an additional axial tensioning after obtaining the engagement between the locking segments and the cavity. The engagement between the locking segments and the cavity is provided by the described back snapping connection already during axial slid on of the connecting element onto the coupling segment without that an initial turning of the two parts with respect to each other is necessary to this end as in case of a usual thread. This combination of axial slid on with engagement of locking segments into the cavity and of consecutive turning of the connecting segment around about ⅛ to ⅞ of the circumference of the coupling segment simplifies manufacturing of such syringes and allows a secure and highly leak tight mechanical positive fitting and frictionally engaging connection between the needle and the syringe body.

It is further proposed that the hull has at its supporting segment a boundary wall, which points radially inwards and through the center of which the needle passes, wherein in an assembled state of the syringe the boundary wall exerts with its inner surface, which faces the syringe body, an axial force onto the sealing elements that lie against an axial front surface of the coupling segment.

To this end, it is conceived as a further embodiment that the supporting segment comprises a stabilizing ring that points radially inwards, which lies in the assembled state of the syringe against the front surface of the coupling segment, wherein preferably the stabilizing ring is formed integrally with the hull.

The sealing elements and the needle are preferably accommodated in the connecting element or in the hull and are preferably fastened therein such that they can be or are connected to the coupling segment of the syringe body as a combined element.

Further, it is proposed that the syringe body and the coupling segment are formed integrally, preferably of glass.

The connecting element or the hull may be formed of synthetic materials.

To allow a precise accommodation of the needle in the connecting segment it is proposed that the needle comprises a needle holder that is accommodated in the connecting element or the hull, which tightly encompasses a syringe body-side end of a cannula of the needle in circumferential direction and is held in the assembled state of the syringe by means of tightening elements between the connecting element or the hull and the needle-side front surface of the coupling segment.

In what follows the invention will be described exemplarily and without limitations with reference to the accompanying figures.

Figure 1:
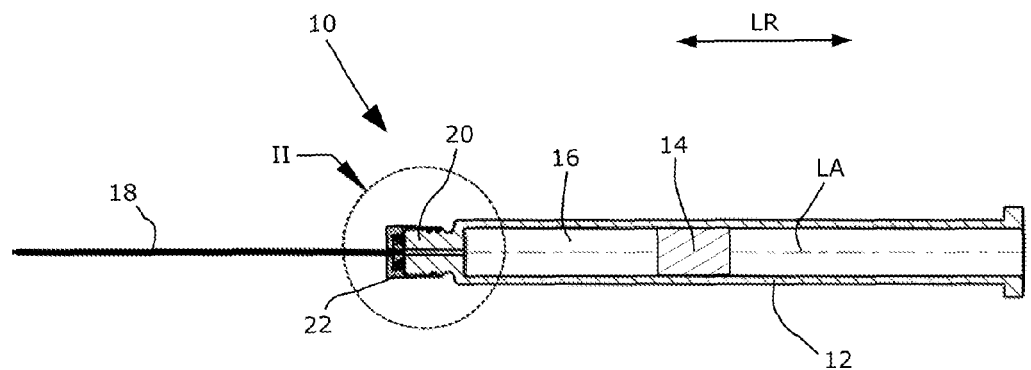
FIG. 1 shows a simplified and schematic longitudinal sectional view of an embodiment of a syringe with syringe body and needle.

In FIG. 1 an embodiment of a syringe 10 is illustrated simplified and schematically in a longitudinal sectional view along the longitudinal axis LA. The syringe 10 comprises a syringe body 12 that accommodates a plunger 14 that can be moved along the longitudinal direction LR. The plunger 14 is connected to not illustrated operation means such that the volume of a receiving space 16 (inner cavity of the syringe body 12) for a fluid, which can be taken in or given off by means of the syringe 10, can be changed. A needle 18 is connected to the syringe body 12. The coupling between the needle 18 and the syringe body 12 is obtained by means of a coupling segment 20, which is provided on the syringe body 12, and a connecting element, which is provided at a needle-side of the syringe body 12 and that is preferably formed as a kind of hull and can be slid on in axial longitudinal direction LR onto the coupling segment 20.

Figure 2:
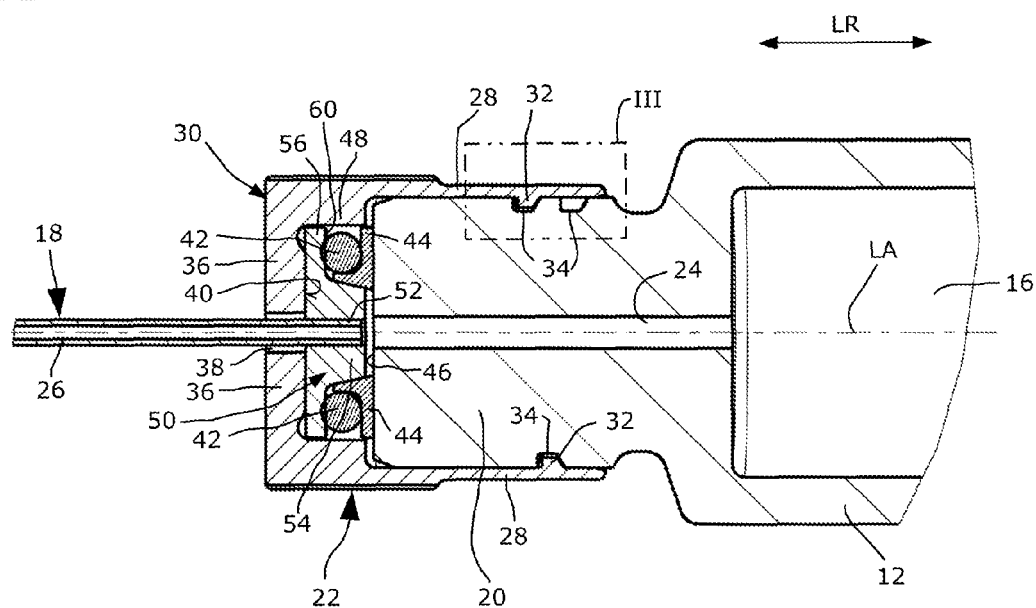
FIG. 2 shows an enlargement of the connecting region between the syringe body and the needle with connecting element and coupling segment that is indicated with II in FIG. 1.

The connection between the needle 18 and the syringe body 12 will now be explained with respect to the enlarged schematic sectional view of FIG. 2, which corresponds substantially to the circular region indicated by II in FIG. 1.

The coupling segment 20 is preferably connected integrally to the syringe body 12. The receiving space 16 forms a fluid connection with a cannula 26 of the needle 18 by means of a channel 24 that is formed within the coupling segment 20, if the connecting element 22 and the needle 18 are connected to the coupling segment 20.

The connecting element 22, to which it will be referred as hull 22 in what follows, comprises a syringe body-side connecting segment 28 and a needle-side supporting segment 30. On the connecting segment 28 at least one locking segment 32 is provided that extends or protrudes radially inwards with respect to the longitudinal axis LA. The locking element(s) 32 engage(s) in an assembled state of the syringe 10 with a cavity 34 that is formed on the coupling segment 20. The cavity 34 and the locking segment(s) 32 have corresponding profiles such that by the engaging of the locking segment(s) 32 and the cavity 34 a positive fitting, mechanical connection between the connecting element 22 and the coupling segment 20 can be or is obtained.

At its supporting segment 30 the connecting element 22 comprises a boundary wall 36 that points radially inwards, in the center of which an opening 38 is provided, through which the needle 18 passes. In the assembled state of the syringe 10 the boundary wall 36 exerts with its inner surface 40 that faces the syringe body an axial force onto sealing elements 42, 44 such that these are pressed against an axial front surface 46 of the coupling segment 20 or such that a pretension is applied to these sealing elements. The supporting segment comprises further a stabilizing ring segment 48 that points radially inwards and that faces in the assembled state of the syringe 10 the front surface 46 of the coupling segment 20. The stabilizing ring 48 is formed preferably integrally with the hull 22.

Further, within the hull 22 a needle holder 50 is provided that tightly encompasses a syringe body-side end 52 of the cannula 26 of the needle 18 in circumferential direction, and that is held in the assembled state of the syringe by means of the sealing elements 42, 44 between the coupling element or the hull 22 and the needle-side front surface 46 of the coupling segment 20. Here, the needle holder 50 comprises a cone 54 that tapers towards the coupling segment 20 and a flange 56 that is connected to the cone 54 at the needle side. The flange 56 extends in radial direction substantially from the cannula 26 of the needle 18 to the inner circumference of the hull 22 and touches with its syringe body-side supporting surface 60 the sealing element 42, which is preferably formed as a ring seal with a circular cross-section.

The sealing element 42 is in turn supported by a further sealing or supporting element 44. This sealing or supporting element 44 has a cone shaped form that corresponds to the cone 54. During axial replacement of the hull 22 and the needle holder 50 accommodated therein in a direction towards the coupling segment 20, the flange 56 exerts forces acting in axial direction onto the sealing elements 42, 44. The cone 54 exerts because of its geometry also forces that comprise radial components such that the sealing elements 42, 44 are advantageously distorted and compressed between the hull 22 and the coupling segment 20, to obtain the desired high leak tightness of the mechanical connection between needle 18 and syringe body 14.

Figure 4:
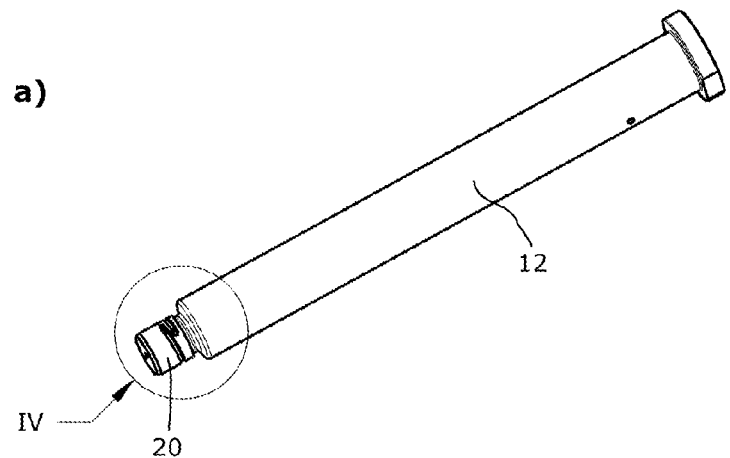
FIG. 4 shows in partial figure a) a schematic and simplified perspective view of the syringe body and in partial figure b) an enlargement of the region indicated with IV of FIG. 3a).
Figure 4:
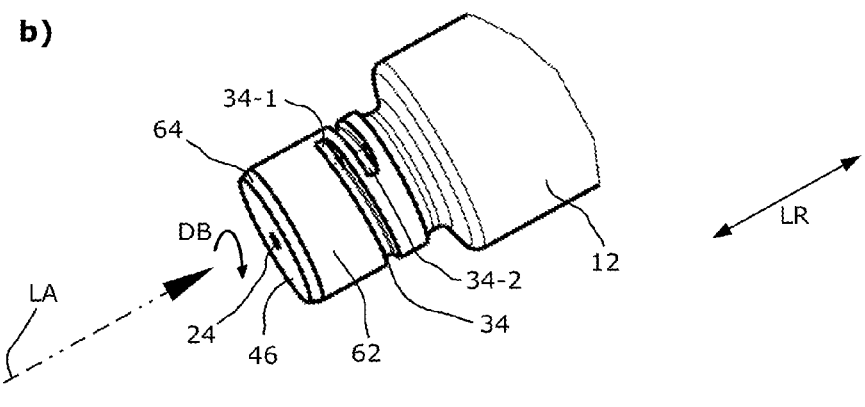

FIG. 4a shows the syringe body 14 in a simplified and schematic perspective view with its coupling segment 20. FIG. 4b is an enlarged view of the coupling segment 20 according to region IV of FIG. 4a. From this view it can be seen that the cavity 34 is formed circumferentially around the coupling segment 20 and has a lead in axial direction. Preferably, the cavity is formed as a thread with two transitions 34-1 and 34-2. The transition 34-1 and 34-2 connect the outer circumferential surface 62 of the coupling segment to the cavity 34. As can be further seen from the view of FIG. 4b the coupling segment comprises next to its needle-side front surface 46 an inclined guiding segment 64 that forms the transition between the front surface 46 and the outer circumferential surface 62. Further in the front surface 46 the channel 24 can be seen that forms the fluid connection to the receiving space in the interior of the syringe body 12.

Figure 5:
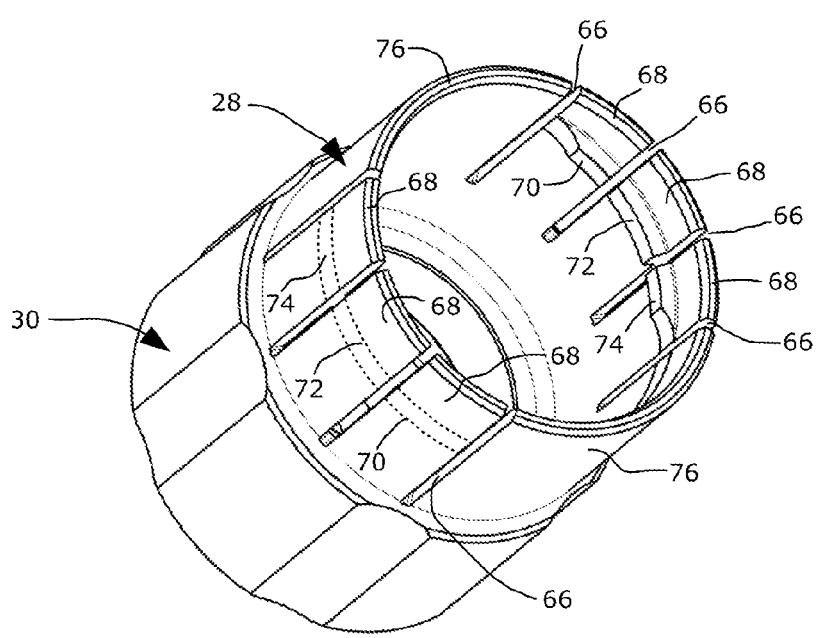
FIG. 5 shows a simplified and schematic perspective view of a connecting element that allows coupling between needle and syringe body.

FIG. 5 shows in schematic, perspective view the connecting element 22 or the hull 22 with the connecting segment 28 and the supporting segment 30. The connecting segment 28 comprises distributed along its circumference several grooves or recesses 66. These grooves 66 form connecting segment parts 68 that are elastically deflectable in radial direction. On the inner circumferential surface of these connecting segment parts 68, to which is may also be referred as connecting latches 68, locking segment parts 70, 72, and 74 are respectively formed that form together a locking segment 32. As can be seen from the view of FIG. 5 in this embodiment two locking segments 32 are formed that are arranged opposite to each other, wherein in the figure the right locking segment 32 can be seen, the left locking segment 32 with its locking segment parts 70, 72, 74 is indicated by a dashed line and cannot be seen. In circumferential direction non-deflectable connecting segment parts 76 lie respectively between the two locking segments 32. In the present example the locking segment parts 76 and each of the two groups of connecting latches 68 extend approximately across a quadrant of the circumferential direction. Obviously, the arrangement of the connecting latches 68 and the connecting segment parts 70 is also conceivable in a different way. For example, also three times one or three times two connecting latches may be arranged with 120° offset with respect to each other, respectively. The number of connecting latches and their distributed arrangement along the circumference can be adapted according to the dimensions of the syringe and the requirements on the desired connection. The example illustrated here with two times three connecting latches 68 is therefore not necessarily limiting with regard to the design of the connecting latches 68 and the locking segments 32 or the locking segment parts 70, 72, 74.

Figure 3:
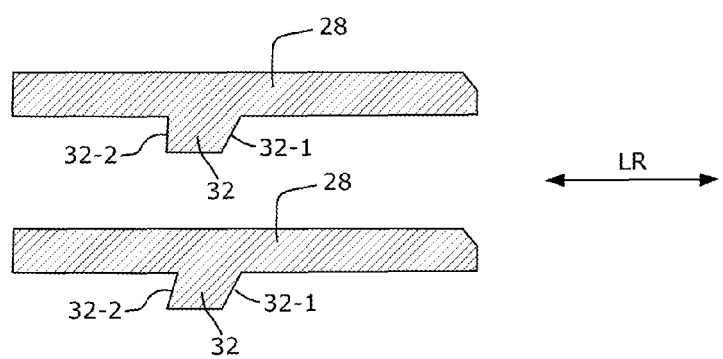
FIG. 3 shows an enlargement of the connecting element and its locking segments according to the region III of FIG. 2 in two alternatives.

With respect to the design of the locking segments 32 it is referred to the schematic and simplified partial view of FIG. 3. In this view a part of the hull 22 is illustrated according to region III of FIG. 2 without the coupling segment 20. In both examples the locking segments 32 have an inclined guiding surface 32-1. Further, both locking segments 32 have supporting surfaces 32-2 facing the needle side. These supporting surfaces 32-2 lie against according side surfaces of the cavity 34 that is preferably formed as thread and support the axially acting forces in the assembled state of the syringe. The upper example shows a supporting surface 32-2 that is aligned substantially orthogonally to the axial longitudinal direction LR. The supporting surface 32-2 of the lower example is inclined relative to the axial direction such that the locking segment 32 has the form of a barbed hook. By a design of the locking segment 32 as shown in the lower example the connection between the connecting element 22 and the coupling segment 20 is further improved in comparison to the substantially orthogonal design (upper example). It is difficult to achieve an accidental release of this mechanical connection in both cases. For the lower example such a release is in particular only possible under influence of forces that lead to breaking off of connecting segment parts or connecting latches 68 or of the locking segment parts 70, 72, 74 (FIG. 5).

Figure 6:
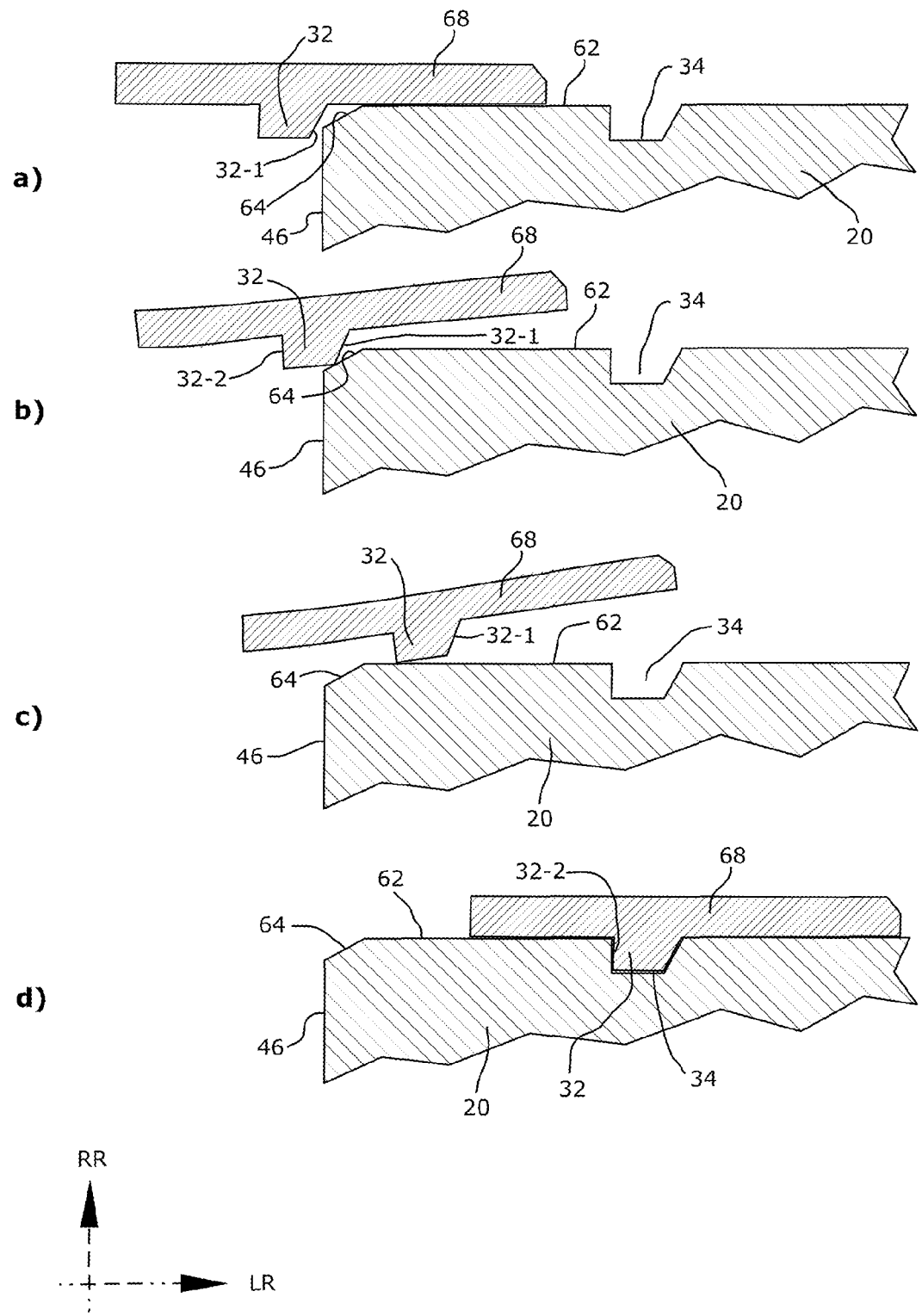
FIG. 6 shows simplified and schematically in a sectional view the process of axial slid on of the connecting element onto the coupling segment and establishment of a locking connection between these elements (steps a-d).

In FIG. 6 illustrates in simplified and schematic manner how the locking or snap back connection between the hull 22 and the coupling segment 20 during slid on of the hull 22 in axial longitudinal direction LR onto the coupling segment 20 is obtained. In the beginning of the process (a) the locking segments 32 come with their guiding surfaces 32-1 into contact to the inclined guiding segment 64 of the coupling segment 20. The inclined surfaces of the locking segments 32 and of the guiding segments 64 have in this process a freely eligible inclination that is chosen such that during an axial movement of the connecting element 22 towards the coupling segment 20 the locking segments 32 are deflected in the radial direction RR by the guiding segment 64 (b). Here, a radial elastic deflection of the connecting latches 68 outwards occurs (FIG. 5). The locking segments 32 lie then against the outer circumferential surface of the coupling segment 20 (c) and engage or snap back into the cavities 34 after a further axial slid on of the hull 22 because of the acting pretension forces caused by the elastic deflection (d). As soon as the locking segments 32 are engaged with the cavities 34 the hull 22 can be tightly connected to the coupling segment 20 by a clock-wise turning movement (see arrow DB in FIG. 5), which amounts preferably to ⅛ up to maximally ⅞ of a full turn, in particular to about ¼ to ⅓ of a full turn. The mechanical or positive fitting and frictionally engaged connection between the hull 22 and the coupling segment 20 is therefore obtained by a combination of an axial slid on including engagement and a subsequent small turning movement. It should be noted in this context that the locking segments 32 are arranged according to the lead of the thread of the cavities 34 in the locking segment 28, i.e. they have also an according lead, for example in the manner of a partial inner thread. The described process for assembling of the completed syringe 10 constitutes a simple joining process in the final assembly that is less time consuming than providing glue connections in combination with thread connections, if necessary, for which several turns of the elements to be connected together with respect to each other are necessary.

Finally, it should also be noted that the syringe body 12 is formed preferably integrally with the coupling segment 20. As material for the syringe body 12 glass is preferred, but also synthetic materials that are suitable for laboratory uses could be used. The connecting element or the hull 22 is preferably formed of synthetic materials that can preferably be used in a temperature range of about +300° C. to −70° C.

In summary, a syringe 10 for laboratory uses, such as chromatography applications, is provided for which the connecting element (hull) 22 and the coupling segment 20 engage in a locking or snap back connection. Here, the locking geometry (locking segments 32, cavity 34) is designed such that after engagement an axial pretension can be applied by tightening the connecting element 22 by means of a partial turn around the longitudinal axis LA. By this axial pretension the sealing or supporting elements 42, 44 that are integrated in the connecting element 22 are pretensioned such that a desired leak tightness of the syringe 10 that is sufficient for laboratory uses can be achieved. The syringe presented herein can in particular be used in high temperature chromatography, head space chromatography, in environments with solvents (no glue that could be damaged), for high purity applications, during which no organic materials are allowed to outgas (of glues), and also for applications during which a large tension acts on the connection between needle and syringe body.

The invention claimed is:

1. A syringe comprising:
   a syringe body (12) having an axial inner cavity (16) and a coupling segment (20) at one longitudinal end thereof, the coupling segment having at least one radially inwardly formed cavity (34);
   a needle (18); and
   a connecting element (22) within which the needle is held, the connecting element being configured to connect the needle to the longitudinal end of the syringe body and comprising:
      a syringe body-side connecting segment (28);
      a needle-side supporting segment (30);
      several locking segments (32) arranged on the connecting segment (28) and configured to engage the cavity of the coupling segment, wherein the locking segments are arranged in a circumferential direction on the connecting segment, extend along an inner circumference of the connecting element (22), and project radially inwards; and
      grooves (66) that extend in a longitudinal direction such that the locking segments (32) comprise several locking segment parts (70, 72, 74) arranged on corresponding connecting segment parts (68), wherein the connecting segment parts (68) can be deflected in a radial direction (RR).

2. Syringe according to claim 1, wherein the syringe further comprises tensioning means for producing an axial pretension between the coupling segment (20) and the connecting element (22), the pretension acting on sealing elements (42, 44), which are accommodated between the coupling segment (20) and the connecting segment (22).

3. Syringe according to claim 2, wherein the tensioning means comprises the at least one cavity (34) on the coupling segment (20), wherein the cavity (34) extends along the circumference of the coupling segment (20) and is formed as a thread.

4. Syringe according to claim 3, wherein the thread is formed such that it has a transition (34-1, 34-2) to an outer circumferential surface (62) of the coupling segment (20) in both turning directions, and configured such that the connecting element (22) is able to turn not more than one turn with respect to the coupling segment (34).

5. Syringe according to claim 1, wherein the connecting element (22) comprises on the needle-side supporting segment (30) a boundary wall (36) that points radially inwards and includes an inner surface (40) that faces the syringe body (12), and through a center of which (38) the needle (18) passes, wherein in an assembled state of the syringe the boundary wall (36) exerts with the inner surface (40) an axial force onto sealing elements (42, 44) that lie against an axial front surface (46) of the coupling segment (20).

6. Syringe according to claim 5, wherein the needle-side supporting segment (30) further comprises a stabilizing ring (48) that points radially inwards, which lies in the assembled state of the syringe (10) against the front surface (46) of the coupling segment (20).

7. Syringe according to claim 2, wherein the sealing elements (42, 44) and the needle (18) are accommodated in the connecting element (22) such that they can be or are connected as a combined element to the coupling segment (20) of the syringe body (12).

8. Syringe according to claim 1, wherein the syringe body (12) and the coupling segment (20) is integrally formed.

9. Syringe according to claim 1, wherein the connecting element (22) is formed of synthetic materials.

10. Syringe according to claim 1, further comprising a needle holder (50) accommodated in the connecting element (22), which tightly encompasses a syringe body-side end (52) of a cannula (26) of the needle (18) in circumferential direction, and which is held in the assembled state of the syringe (10) by means of sealing elements (42, 44) between the connecting element (22) and an axial front surface (46) of the coupling segment (20).

11. Syringe according to claim 4, wherein the thread is formed such that the connecting element (22) is able to turn about ⅛ to ⅞ of the circumference of the coupling segment (20).

12. Syringe according to claim 6, wherein the stabilizing ring (48) is formed integrally with the connecting element (22).

13. Syringe according to claim 8, wherein the syringe body (12) and the coupling segment (20) are integrally formed of glass.

* * * * *